United States Patent [19]

Enomoto et al.

[11] Patent Number: 4,931,391

[45] Date of Patent: Jun. 5, 1990

[54] METHOD FOR PRESERVATION OF NITRILE HYDRATION ACTIVITY

[75] Inventors: Kanehiko Enomoto, Tokyo; Koitchiro Ryuno; Hitoshi Shimizu, both of Yokohama, all of Japan

[73] Assignees: Mitsubishi Rayon Kabushiki Kaisha; Nitto Kagaku Kogyo Kabushiki Kaisha, both of Tokyo, Japan

[21] Appl. No.: 45,869

[22] Filed: May 1, 1987

[30] Foreign Application Priority Data

May 2, 1986 [JP] Japan ................................ 61-101044

[51] Int. Cl.$^5$ ............................................. C12N 9/96
[52] U.S. Cl. ................................. 435/188; 435/227; 435/832; 435/840; 435/843; 435/859; 435/872
[58] Field of Search ............... 435/188, 227, 843, 832, 435/872, 859, 840

[56] References Cited

U.S. PATENT DOCUMENTS 4,390,631 6/1983 Watanabe et al. .................. 435/227
4,629,700 12/1986 Prevatt et al. ....................... 435/227

FOREIGN PATENT DOCUMENTS 0115781 8/1984 European Pat. Off. ............ 435/227
0137076 4/1985 European Pat. Off. ............ 435/227

OTHER PUBLICATIONS

Bui et al., "A Note on the Enzymic Action and Biosynthesis of a Nitrile-Hydratase from a Brevibacterium sp.," J. Appl. Bacterial. 1984, 57(1), 183-190, (CA 101:166185t).

Fradet et al., "Hydratation of Nitriles Using a Bacterial Nitrile-Hydratase Immobilized on DEAE-Cellulose," Biotechnol. and Bioeng., vol. 27, No. 11, pp. 1581-1585, (1985).

Nagasawa et al., "Nitrile Hydratase of Pseudomonas Chlororaphis B23," Eur. J. Biochem., 162, 619-698, (Feb. 1987).

*Primary Examiner*—Robert A. Wax
*Attorney, Agent, or Firm*—Emmanuel J. Lobato; Robert E. Burns

[57] ABSTRACT

Nitrile hydration activity of the nitrilase or the immobilized form thereof can be stably preserved by adding as a stabilizer at least one compound selected from nitriles, amides, and organic acids and salts thereof to a solution or suspension of the nitrilase or of the immobilized form thereof.

4 Claims, No Drawings

METHOD FOR PRESERVATION OF NITRILE HYDRATION ACTIVITY

BACKGROUND OF THE INVENTION

The present invention relates to a method for prevention of reduction with elapse of time in nitrile hydration activity of nitrilase produced by a specific microorganism and for stable preservation of this activity.

In recent years, the technology of immobilized enzymes and microorganisms has developed rapidly, resulting in increasing attempts to utilize microorganisms and enzymes as they are or in the immobilized state as catalysts for various single or complex chemical reactions.

Nitrilase has been known as an enzyme capable of hydrating nitriles to produce the corresponding amides. As examples of the utilization of this enzyme, methods for producing (meth)acrylamide from (meth)acrylonitrile with the use of microorganisms of the genus Corynebacterium or Nocardia which produce nitrilase (Reference: Japanese Patent Pub. No. 17918/1981); for producing from $C_{2-4}$ nitriles the corresponding amides with the use of microorganisms of the genus Rhodococcus (Reference: Japanese Patent Appln. No. 452/1985); and for producing from nitriles the corresponding amides with the use of microorganisms of the genus Bacillus, Bacteridium, Micrococuss or Brevibacterium (Reference: Japanese Patent Laid-Open Pub. No. 86186/1976) have been proposed.

As a result of further investigation, however, we have found that the nitrile hydration activity of the above mentioned nitrilase is labile and decreases as the temperature rises or the purity of the enzyme increases. This decrease occurs also with immobilized enzymes.

SUMMARY OF THE INVENTION

As a result of extensive research effort expended toward solving the above problems and efficiently utilizing the nitrile hydration activity of nitrilase, we have found that the use of specific substances, i.e., nitriles, amides and organic acids or salts thereof, is very effective for this purpose and have arrived at the present invention on the basis of this finding.

More specifically, the present invention provides a method for preservation of the nitrile hydration activity of nitrilase produced by a Gram-positive microorganism or of an immobilized form thereof, both having nitrile hydration activity, which method comprises adding as a stabilizer at least one compound selected from the group consisting of nitriles, amides, and organic acids and salts thereof to a solution or suspension of said nitrilase or of said immobilized form thereof.

DETAILED DESCRIPTION OF THE INVENTION

Microorqanism:

The microorganisms used in the present invention are specific ones capable of producing nitrilase and hydrating nitriles, especially acrylonitrile, to produce the corresponding amides, especially acrylamide. Specific examples of such microorganisms are strains N-771(FERM P-4445) and N-774(FERM P-4446) of the genus Corynebacterium and strain N-775(FERM P-4447) of the genus Nocardia disclosed in Japanese Patent Pub. No. 17918/1981 mentioned above, strain sp. S-6(FERM BP-687) of the genus Rhodococcus disclosed in Japanese Patent Appln. No. 452/1985 again mentioned above, and strains of the genera Bacillus, Bacterium, Micrococcus and Brevibacterium disclosed in Japanese Patent Laid-Open Pub. No. 86186/1976 mentioned previously.

Cultivation of these microorganisms is ordinarily carried out under aerobic conditions by inoculating strains of the respective microorganisms into culture media containing: carbon sources such as glucose, sucrose, dextrins, and glycerol; nitrogen sources such as ammonium sulfate and urea; organic nutrient sources such as yeast extract, meat extract, malt extract, and peptone; and other optional ingredients.

The pH of the culture medium is of the order of 5 to 9, preferably of the order of 6 to 8, while the cultivation temperature is of the order of 20° to 37° C., preferably of the order of 20° to 30° C., and the cultivation time is about 1 to 3 days. Cells obtained by the cultivation can be collected for example, by centrifugation.

Nitrilase:

The nitrilase used in the present invention is an enzyme produced by the aforementioned microorganism, and irradiation with light rays is required in order to induce its activity to the fullest extent (Reference: Japanese Patent Appln. No. 2724/1985). This enzyme can be separated and extracted by the following procedure.

First, the cells collected from the culture fluid by centrifugation and the like are suspended in a buffer in a quantity sufficient to reach a given cell concentration and crushed in an ultrasonic cell crusher, Daino mill or French press. Uncrushed cells and cell walls or membranes are removed, for example, by centrifugation to obtain a soluble fraction (cell extract). The cell extract thus obtained is purified by a conventional method such as ammonium sulfate fractionation, DEAE-Sephacel Phenyl-Sepharose ® or Sephadex ® column chromatography or crystallization whereby a partly purified enzyme solution or a purified enzyme (solution) can be obtained.

Both these enzymes can be used in the present invention irrespective of whether they are purified partly or completely.

Immobilized Enzyme:

The immobilized enzymes of the present invention can be obtained by subjecting the above stated nitrilase to the adsorption method which involves adsorption onto activated carbon and the like, the ionic bond method which involves bonding to ion exchange resins and the like, the covalently bonding method which involves covalently bonding to glass beads, and the entrapping method which involves entrapping with acrylamide, carrageenan, alginate and the like in accordance with a conventional method.

Stabilizer:

The stabilizers used in the present invention are compounds selected from nitriles, amides, and organic acids and salts thereof, and these compounds can be used singly or in combination.

Specific examples of such compounds are:

(1) Aliphatic nitriles such as acetonitrile, propionitrile and isobutyronitrile and the corresponding amides and acids or salts thereof.

(2) Aminonitriles such as glycine nitrile, α-aminopropionitrile and β-aminopropionitrile and the corresponding amides and acids or salts thereof.

(3) Hydroxynitriles such as lactonitrile, hydroxyacetonitrile and β-hydroxypropionitrile and the corresponding amides and acids or salts thereof.

(4) Unsaturated nitriles such as acrylonitrile and methacrylonitrile and the corresponding amides and acids or salts thereof.
(5) Dinitriles such as malononitrile, succinonitrile and adiponitrile and the corresponding diamides and dibasic acids or salts thereof.
(6) Monocyanoamides and monocyanic acids such as cyanoacetamide and cyanoacetic acid or salts thereof.
(7) Aromatic nitriles such as benzonitrile and phenylacetonitrile and the corresponding amides and acids or salts thereof.
(8) Heterocyclic nitriles such as nicotinonitrile and isonicotinonitrile and the corresponding amides and acids or salts thereof.
(9) Halogenated nitriles such as chloroacetonitrile and β-chloropropionitrile and the corresponding amides and acids or salts thereof.
(10) Acids having an aldehyde group such as glyoxylic acid or salts thereof.

Preservation of Nitrile Hydration Activity:

The preservation of nitrile hydration activity can be attained by adding any of the above enumerated compounds to a solution or suspension of the previously mentioned nitrilase or an immobilized form thereof dissolved or dispersed in various buffers or physiological saline. Ordinarily, the quantity of the stabilizer added is in the range of from 0.01 to 50 g/l but 0.1 to 10 g/l of the stabilizer is preferably added from the point of view of storage stability, cost and the like.

The pH of the solution or suspension is 5 to 8, preferably 5.5 to 7, and a variety of buffers such as phosphate buffer and Tris buffer are ordinarily employed. In some cases, it may be effective to control pH by adding an acid such as hydrochloric acid or sulfuric acid or an alkali such as caustic soda or caustic potash.

While the solution or suspension thus obtained may be stored at room temperature as long as the storage period is short, storage at a low temperature, especially at a temperature in the vicinity of 0° C. is preferred.

In accordance with the present invention, nitrile hydration activity can be preserved stably over a long period of time. This effect is observed not only in the storage stability of the enzyme solution at the respective stages of the enzyme purification described previously but also in the preservation of the enzyme activity in each purification step. It is therefore preferable that the stabilizer be added to the enzyme solution or buffer used in each purification step.

In order to indicate more fully the nature and utility of this invention, the following specific examples of practice are set forth, it being understood that these examples are presented as illustrative only and not intended to limit the scope of the invention.

EXPERIMENTAL EXAMPLES

In each of the following experimental examples, 0.1 ml of an enzyme solution was charged into a beaker containing 9.9 ml of phosphate buffer and irradiated with a 100-W EYE LAMP (supplied by Toshiba, Japan) positioned at a distance of 50 cm for 30 minutes in a bath maintained at 10° C. to induce the enzyme activity to the fullest extent. The resulting solution was then added to 10 ml of M/20 phosphate buffer (pH 7.7) containing 5.0% by weight of acrylonitrile to cause reaction at 10° C. for 10 minutes. The nitrile hydration activity of the test enzyme solution was determined by measuring the quantity of acrylamide produced by gas chromatography, the capability of producing 1μ mole of acrylamide per ml of the enzyme solution per minute being designated as 1 unit (U).

EXAMPLE 1 AND COMPARISON EXAMPLE 1

A culture medium comprising 10 g/l of glucose, 5 g/l of peptone, 3 g/l of yeast extract, and 3 g/l of malt extract was adjusted to a pH of 7.2, and 100 ml of the resulting culture medium was sterilized in a 500-ml Erlenmeyer flask.

After cooling, the sterilized culture medium was inoculated with 1 ml of a culture fluid obtained by precultivating strain N-774(FERM P-4446) of the genus Corynebacterium in the same culture medium as is described above for 2 days, and cultivation was carried out aerobically at 30° C. for 2 days.

Cells were separated from the culture fluid by centrifugation (3° C., 10,000 rpm, 20 minutes) and washed with a physiological saline. The washed cells were subjected to centrifugation under the same conditions and then suspended in a physiological saline to obtain a suspension of washed cells.

Subsequently, 50 ml of this cell suspension was mixed with 50 ml of M/10 phosphate buffer (pH 6.5) containing 10 g/l of ammonium isobutyrate ($2.5 \times 10^3$ U/ml).

The resultant cell suspension was pressed in a French press (fabricated by Ohtake Seisaku-sho, Japan) to crush cells under a pressure of 1,000 to 1,500 kg G and then subjected to centrifugation (12,000 rpm, 30 minutes) to remove uncrushed cells and insolubles such as cell walls, whereby a cell extract, i.e. a crude enzyme solution, was obtained.

For comparison purposes, a similar cell suspension ($2.5 \times 10^3$ U/ml) which contained no ammonium isobutyrate was prepared and subjected to a French press treatment and centrifugation under similar conditions, whereby a control cell extract was obtained.

Both cell extracts were left standing for 2 days at 20° C., and the nitrile hydration activity levels were measured before and after the extracts were left standing. The residual nitrile hydration activity percent (in Table 1, as in all succeeding tables, abbreviated to % residual activity) was calculated on the basis of the data thus obtained. The results are shown in Table 1.

TABLE 1

| Experimental Example | Ammonium Isobutyrate | Activity Before Being Left Standing (U/ml) | Activity After Being Left Standing (U/ml) | % Residual Activity |
|---|---|---|---|---|
| Example 1 | Added | $1.3 \times 10^3$ | $1.2 \times 10^3$ | 92 |
| Comparison Example 1 | None | $1.2 \times 10^3$ | $0.33 \times 10^3$ | 28 |

EXAMPLES 2 THROUGH 6 AND COMPARISON EXAMPLES 2 THROUGH 6

Each aliquot of a suspension of cells of a genus as shown in Table 2 prepared as in Comparison Example 1 was subjected to French press treatment and centrifugation similarly as in Comparison Example 1, whereby a cell extract was obtained.

The cell extract thus obtained was divided into two aliquots, 1 ml of one aliquot being mixed with 1 ml of M/10 phosphate buffer (pH 6.5) containing 10 g/l of ammonium isobutyrate, and 1 ml of the other aliquot being mixed with 1 ml of M/10 phosphate buffer (pH 6.5) as a comparison example. Both solutions were left standing for 2 days at 20° C., and the nitrile hydration activity levels were measured before and after each of the solutions were left standing to calculate % residual activity. The results obtained are summarized in Table 2.

TABLE 2

| Experimental Example | | Genus | Strain | % Residual Activity |
|---|---|---|---|---|
| Example | 2 | Bacillus | CBS-494 | 83 |
| | 3 | Bacteridium | CBS-496 | 78 |
| | 4 | Micrococcus | CBS-497 | 91 |
| | 5 | Brevibacterium | CBS-717 | 89 |
| | 6 | Nocardia | N-775 | 93 |
| Comparison Example | 2 | Bacillus | CBS-494 | 23 |
| | 3 | Bacteridium | CBS-496 | 26 |
| | 4 | Micrococcus | CBS-497 | 30 |
| | 5 | Brevibacterium | CBS-717 | 22 |
| | 6 | Nocardia | N-775 | 24 |

EXAMPLES 7 THROUGH 27 AND COMPARISON EXAMPLE 7

To each 2.5-ml aliquot of a cell extract ($0.8 \times 10^3$ U/ml) prepared as in Comparison Example 1, was added 2.5 ml of M/10 phosphate buffer containing 10 mg of a nitrile as shown in Table 3. The pH of the solution was adjusted to 6.5, and the resulting solution was then left standing at 20° C. for 2 days. The % residual activity was calculated similarly as in the preceding Examples, whereupon the results set forth in Table 3 were obtained.

TABLE 3

| Experimental Example | | Nitrile Added | % Residual Activity |
|---|---|---|---|
| Comparison Example | 7 | None | 21 |
| Example | 7 | Acetonitrile | 61 |
| | 8 | Propionitrile | 83 |
| | 9 | n-Butyronitrile | 93 |
| | 10 | Isobutyronitrile | 88 |
| | 11 | n-Valeronitrile | 82 |
| | 12 | n-Capronitrile | 71 |
| | 13 | Glycine nitrile | 58 |
| | 14 | β-Aminopropionitrile | 55 |
| | 15 | Lactonitrile | 49 |
| | 16 | β-Hydroxypropionitrile | 78 |
| | 17 | Acrylonitrile | 56 |
| | 18 | Methacrylonitrile | 62 |
| | 19 | Malononitrile | 55 |
| | 20 | Succinonitrile | 70 |
| | 21 | Adiponitrile | 68 |
| | 22 | Cyanoacetamide | 53 |
| | 23 | Cyanoacetic acid | 54 |
| | 24 | Benzonitrile | 44 |
| | 25 | Nicotinonitrile | 43 |
| | 26 | Chloroacetonitrile | 58 |
| | 27 | β-Chloropropionitrile | 63 |

EXAMPLES 28 THROUGH 45 AND COMPARISON EXAMPLE 8

The procedures of Examples 7 through 27 were followed except that the nitriles added were replaced by amides. The results obtained are presented in Table 4.

TABLE 4

| Experimental Example | | Amide Added | % Residual Activity |
|---|---|---|---|
| Comparison Example | 8 | None | 21 |
| Example | 28 | Acetamide | 57 |
| | 29 | Propionamide | 83 |
| | 30 | n-Butyramide | 90 |
| | 31 | Isobutyramide | 85 |

TABLE 4-continued

| Experimental Example | Amide Added | % Residual Activity |
|---|---|---|
| 32 | n-Valeramide | 78 |
| 33 | n-Capronamide | 75 |
| 34 | Glycine amide | 49 |
| 35 | β-Aminopropionamide | 52 |
| 36 | Lactamide | 50 |
| 37 | β-Hydroxypropionamide | 61 |
| 38 | Acrylamide | 63 |
| 39 | Methacrylamide | 70 |
| 40 | Malondiamide | 48 |
| 41 | Succindiamide | 63 |
| 42 | Benzamide | 47 |
| 43 | Nicotinamide | 39 |
| 44 | Chloroacetamide | 60 |
| 45 | β-Chloropropionamide | 68 |

EXAMPLES 46 THROUGH 62 AND COMPARISON EXAMPLE 9

The procedures of Examples 7 through 27 were followed except that the nitriles added were replaced by organic acids and that the pH of the solution was adjusted to 6.5. The results obtained are set forth in Table 5.

TABLE 5

| Experimental Example | | Organic Acid Added | % Residual Activity |
|---|---|---|---|
| Comparison Example | 9 | None | 21 |
| Example | 46 | Formic acid | 48 |
| | 47 | Acetic acid | 55 |
| | 48 | Propionic acid | 78 |
| | 49 | Isobutyric acid | 83 |
| | 50 | Valeric acid | 81 |
| | 51 | Caproic acid | 78 |
| | 52 | β-Aminopropionic acid | 45 |
| | 53 | Malic acid | 43 |
| | 54 | Glycolic acid | 52 |
| | 55 | DL-Glyceric acid | 60 |
| | 56 | Oxalacetic acid | 68 |
| | 57 | Succinic acid | 59 |
| | 58 | Benzoic acid | 48 |
| | 59 | Monochloroacetic acid | 39 |
| | 60 | Glyoxylic acid | 72 |
| | 61 | Acrylic acid | 53 |
| | 62 | Methacrylic acid | 59 |

EXAMPLES 63 THROUGH 75 AND COMPARISON EXAMPLES 10 THROUGH 13

To each 2.5 ml aliquot of a cell extract ($1 \times 10^3$ U/ml) prepared as in Comparison Example 1, was added 2.5 ml of M/10 phosphate buffer containing 25 mg of a stabilizer as shown in Table 6. The pH of the solution was adjusted to a predetermined level, and the resulting solution was left standing at 20° C. for 2 days.

The nitrile hydration activity levels was measured before and after each of the solutions was left standing to calculate % residual activity. The results obtained are summarized in Table 6.

TABLE 6

| Experimental Example | | Stabilizer Added | pH | % Residual Activity |
|---|---|---|---|---|
| Comparison Example | 10 | None | 5.0 | 4 |
| | 11 | " | 6.0 | 13 |
| | 12 | " | 7.0 | 27 |
| | 13 | " | 8.0 | 32 |
| Example | 63 | Isobutyronitrile | 5.0 | 3 |
| | 64 | " | 6.0 | 82 |
| | 65 | " | 7.0 | 77 |

TABLE 6-continued

| Experimental Example | | Stabilizer Added | pH | % Residual Activity |
|---|---|---|---|---|
| | 66 | " | 8.0 | 45 |
| Example | 67 | Isobutyramide | 5.0 | 4 |
| | 68 | " | 6.0 | 80 |
| | 69 | " | 7.0 | 74 |
| | 70 | " | 8.0 | 48 |
| Example | 71 | Isobutyric acid | 5.0 | 2 |
| | 72 | " | 5.5 | 82 |
| | 73 | " | 6.0 | 83 |
| | 74 | " | 7.0 | 77 |
| | 75 | " | 8.0 | 42 |

EXAMPLES 76 THROUGH 92 AND COMPARISON EXAMPLE 14

To each 2.5-ml aliquot of a cell extract ($0.7 \times 10^3$ U/ml) prepared as in Comparison Example 1, was added 2.5 ml of M/10 phosphate buffer containing a predetermined quantity of a stabilizer as shown in Table 7. The pH of the solution was adjusted to 6.0 (6.5 for the solution containing no stabilizer), and the resulting solution was then left standing at 20° C. for 2 days.

The nitrile hydration activity levels were measured before and after each of the solutions was left standing to calculate % residual activity. The results are set forth in Table 7.

TABLE 7

| Experimental Example | | Stabilizer Added | Concentration (g/l) | % Residual Activity |
|---|---|---|---|---|
| Comparison Example | 14 | None | — | 17 |
| Example | 76 | Butyronitrile | 0.01 | 60 |
| | 77 | " | 0.1 | 82 |
| | 78 | " | 1.0 | 88 |
| | 79 | " | 5.0 | 86 |
| | 80 | " | 20 | 70 |
| Example | 81 | Butyramide | 0.01 | 60 |
| | 82 | " | 0.1 | 85 |
| | 83 | " | 1.0 | 85 |
| | 84 | " | 5.0 | 89 |
| | 85 | " | 20 | 78 |
| | 86 | " | 50 | 63 |
| Example | 87 | Butyric acid | 0.01 | 63 |
| | 88 | " | 0.1 | 87 |
| | 89 | " | 1.0 | 92 |
| | 90 | " | 5.0 | 90 |
| | 91 | " | 20 | 85 |
| | 92 | " | 50 | 67 |

Concentration: Concentration of the stabilizer in the solution left standing

EXAMPLE 93 AND COMPARISON EXAMPLE 15

40 ml of a cell extract prepared as in Example 1, 4.5 g of acrylamide, 0.5 g of N,N'-methylenebisacrylamide, and 40 ml of M/20 phosphate buffer (containing 10 g/l of ammonium isobutyrate, pH 6.0) were mixed to form a homogeneous suspension. To this suspension were added 5 ml of a 5% aqueous solution of dimethylaminopropionitrile and 10 ml of a 1.0% aqueous solution of potassium persulfate, and the mixture was maintained at 10° C. for 30 minutes to cause polymerization. A mass of cell-containing gel obtained was crushed into small particles, which were thoroughly washed with M/20 phosphate buffer containing 5 g/l of ammonium isobutyrate, pH 7.0, whereby approximately 90 g of an immobilized enzyme was obtained.

The washed, immobilized enzyme thus obtained was placed in the same buffer containing 5 g/l of isobutyric acid and left standing at 20° C. for 3 days.

For comparison purposes, the enzyme was immobilized and washed similarly but with the use of phosphate buffer containing no ammonium isobutyrate, and the resultant immobilized enzyme was left standing at 20° C. for 5 days.

The nitrile hydration activity levels of the gel samples were measured as follows before and after the respective immobilized enzymes were left standing.

1 g of immobilized gel was mixed with 5 g of acrylonitrile and 97 ml of M/20 phosphate buffer (pH 7.7), and the mixture was subjected to reaction at 0° C. for 20 minutes with stirring. The quantities of acrylamide in the respective reaction solutions were determined by gas chromatography. The results obtained are set forth in Table 8.

TABLE 8

| Experimental Example | Ammonium Isobutyrate | Quant. of AA produced (%) before enzyme was left standing | Quant. of AA produced (%) after enzyme was left standing |
|---|---|---|---|
| Example 93 | Immobilized with addition of isobutyric acid + Left standing in buffer containing isobutyric acid | 0.71 | 0.60 |
| Comparison Example 15 | None | 0.51 | 0.26 |

What we claim is:

1. A method for preservation of the nitrile hydration activity of nitrilase produced by a Gram-positive microorganism or of an immobilized form thereof, both having nitrile hydration activity, said method comprising admixing as a stabilizer at least one compound selected from the group consisting of nitriles, amides, and organic acids and salts thereof with a solution or suspension of said nitrilase or of said immobilized form thereof, concentration of the nitrile amide and organic acid or the salt thereof in the solution or suspension being in the range of from 0.1 to 50 g/l, and the microorganism being selected from those of the genera Corynebacterium, Nocardia, Rhodococcus, Bacillus, Bacteridium, and Micrococcus.

2. A method as claimed in claim 1, wherein the pH of the solution or suspension is in the range of from 5 to 8.

3. A method as claimed in claim 2, wherein the pH of the solution or suspension is in the range of from 5.5 to 7.

4. A method according to claim 1, in which the stabilizer compound selected from nitriles, amides, and organic acids and salts thereof, comprises compounds used singly or in combination, the compounds comprising:

(a) Aliphatic nitriles comprising acetonitrile, propionitrile and isobutyronitrile and corresponding amides and acids or salts thereof;

(b) Aminonitriles comprising glycine nitrile, α-aminopropionitrile and β-aminopropionitrile and corresponding amides and acids or salts thereof;

(c) Hydroxynitriles comprising lactonitrile, hydroxyacetonitrile and β-hydroxypropionitrile and corresponding amides and acids or salts thereof;

(d) Unsaturated nitriles comprising acrylonitrile and methacrylonitrile and corresponding amides and acids or salts thereof;

(e) Dinitriles comprising malononitrile, succiononitrile and adiponitrile and corresponding diamides and dibasic acids or salts thereof;

(f) Monocyanoamides and monocyanic acids comprising cyanoacetamide and cyanoacetic acid or salts thereof;

(g) Aromatic nitriles comprising benzonitrile and phenylacetonitrile and corresponding amides and acids or salts thereof;

(h) Heterocyclic nitriles comprising nicotinonitrile and isonicotinonitrile and corresponding amides and acids or salts thereof;

(i) Halogenated nitriles comprising chloroacetonitrile and $\beta$-chloropropionitrile and corresponding amides and acids or salts thereof; and (j) acids having an aldehyde group comprising glyoxylic acid or salts thereof.

* * * * *